(12) United States Patent
Divoux et al.

(10) Patent No.: US 8,114,089 B2
(45) Date of Patent: Feb. 14, 2012

(54) INSTRUMENT FOR GRIPPING A CUP COMPONENT OF A JOINT PROSTHESIS

(75) Inventors: Laurent Divoux, Renauvoid (FR); Laurent Zanchin, St. Priest Cedex (FR)

(73) Assignee: Depuy (Ireland) (IE)

( * ) Notice: Subject to any disclaimer, the term of this patent is extended or adjusted under 35 U.S.C. 154(b) by 219 days.

(21) Appl. No.: 12/527,522

(22) PCT Filed: Jan. 3, 2008

(86) PCT No.: PCT/IB2008/000007
§ 371 (c)(1),
(2), (4) Date: Jan. 7, 2010

(87) PCT Pub. No.: WO2008/099242
PCT Pub. Date: Aug. 21, 2008

(65) Prior Publication Data
US 2010/0152743 A1    Jun. 17, 2010

(30) Foreign Application Priority Data
Feb. 15, 2007  (GB) .................................. 0702945.7

(51) Int. Cl.
A61B 17/58 (2006.01)
A61B 17/60 (2006.01)
A61F 2/00 (2006.01)

(52) U.S. Cl. ......................................................... 606/91

(58) Field of Classification Search .................... 606/91, 606/99
See application file for complete search history.

(56) References Cited

U.S. PATENT DOCUMENTS

| | | | |
|---|---|---|---|
| 1,560,048 A | 11/1925 | Fingerle | |
| 2,514,641 A | 7/1950 | Harris, Sr. | |
| 5,540,697 A | 7/1996 | Rehmann | |
| 2005/0137603 A1 | 6/2005 | Belew | |

FOREIGN PATENT DOCUMENTS

| | | |
|---|---|---|
| EP | 1570815 A1 | 9/2005 |
| FR | 2715830 A1 | 8/1995 |
| FR | 2830746 A1 | 4/2003 |
| WO | WO 9511641 A1 | 5/1995 |
| WO | WO 2004010882 A1 | 2/2004 |
| WO | WO 2004069107 A1 | 8/2004 |

OTHER PUBLICATIONS

PCT International Search Report PCT/IB2008/000007 dated May 30, 2008.
UK Search Report GB0702945.7 dated May 22, 2007.
Chagneau Francis, et al.; French patent FR2715830; Aug. 11, 1995; English Abstract; Derwent World Patents Index; 2009 Derwent Information Ltd; Dialog file No. 351 Accession No. 7226715.
Crepin, P.; French patent FR2830746; Apr. 18, 2003; English Abstract; Derwent World Patents Index; 2009 Derwent Information Ltd; Dialog file No. 351 Accession No. 13308818.

*Primary Examiner* — Thomas C. Barrett
*Assistant Examiner* — Sameh Boles

(57) ABSTRACT

An instrument for gripping a cup component of an orthopaedic joint prosthesis comprises a drive plate having a spiral track formed on it and at least two jaw members. Each of the jaw members has a formation on it which can engage the spiral track, and a guide in which the jaw member is a sliding fit. The formations on the jaw members cause the jaw members to translate in their respective guides when the drive plate is rotated.

5 Claims, 2 Drawing Sheets

INSTRUMENT FOR GRIPPING A CUP COMPONENT OF A JOINT PROSTHESIS

The present application is a national stage entry of, International Patent Application PCT/IB2008/000007 filed Jan. 3, 2008.

This invention relates to an instrument for gripping a cup component of an orthopaedic joint prosthesis.

Certain orthopaedic joint prostheses include a hollow cup with an inner surface which defines a generally hemispherical hollow region, and another component which has a spherical part which can be received in the hollow region for articulation relative to the cup component. Such joint prostheses can include hip joint prostheses and shoulder joint prostheses. The exterior of the cup will contact the prepared surface of the patient's bone in which the component is to be implanted. The interior of the cup will present a smooth bearing surface to the spherical part of the other component of the joint prosthesis. The bearing surface can be provided by a single piece cup component. Alternatively, the cup component can comprise a bearing part which provides the bearing surface, and which fits into a shell part. The bearing part can be made from a material which is different from the material of the shell part: for example the bearing part can be made from a polymeric material (such as polyethylene) and the shell part (and the spherical part of the other component) can be made from a metal (such as a cobalt-chromium based alloy, or a stainless steel, or a titanium based alloy).

It is important that the components of an orthopaedic joint prosthesis are positioned accurately in a patient's bone. Both location and alignment are important. Accurate positioning of a component requires that the component be engaged by an appropriate instrument, allowing considerable force to be applied to the component if and as necessary. However, it can be important not to contact the external surface or the internal surface or both of the component with the instrument, especially the internal surface when it has been provided with a smooth polished bearing surface. Scratching or otherwise damaging that surface can impair the bearing properties of the prosthesis.

WO-A-2004/069107 discloses an instrument for gripping a cup component of an orthopaedic joint prosthesis which comprises a plurality of flange members which are biassed outwardly where they can engage a groove on the internal surface of a cup component. The flange members can be displaced inwardly against a biassing force by means of pins which can be forced into off-centre holes in the flange members.

The present invention provides an instrument for gripping a cup component of an orthopaedic joint prosthesis, which of a drive plate having a spiral track formed on it which can be engaged by formations on two or more jaw members, which can be rotated relative to the guides for the jaw members so that the rotation of the drive plate causes the jaw members to translate within their respective guides.

Accordingly, in one aspect, the invention provides an instrument for gripping a cup component of an orthopaedic joint prosthesis, which comprises:
a. a drive plate having a spiral track formed on it,
b. at least two jaw members, each of the jaw members having a formation on it which can engage the spiral track,
c. a guide for each of the jaw members, each jaw member being a sliding fit within its respective guide,
in which the formations on the jaw members cause the jaw members to translate in their respective guides when the drive plate is rotated.

The instrument of the invention has the advantage that the range of movement of the jaw members can be wide, by appropriate design of the drive plate. This allows the instrument of the invention to be used on cup components having a wide range of sizes. Furthermore, it allows some savings on interface components which might otherwise be needed between the instrument and the cup component itself to satisfy wide range of sizes.

The instrument of the invention has the advantage that the jaw members are driven positively, both inwardly and outwardly. This can facilitate use of the instrument, both when moving the jaws to grip a cup component and when moving the jaws to release a cup component.

The instrument of the invention has the advantage that it a cup component can be fitted to it without having to apply an axial force to the cup component towards the instrument.

This can allow the cup component to be fitted to the instrument without having to hold the cup component, so that the fitting step can be performed by a user holding just the instrument. The cup component might for example be sitting in packaging which has been opened. This has the advantage of convenience for the user. It can also help to minimise the risk of damage to the cup component for example as a result of being dropped.

The instrument can include a body assembly which provides the guides for the jaw members. For example, the body assembly can define guides in the form of channels in which the jaw members can slide. The body member can conveniently be formed by a moulding or casting process, or by machining, or by a combination of such steps.

Preferably, the body member has a surface which is directed away from the cup component when the instrument is in use which can be used to apply force to the instrument and to a cup component which is engaged by the instrument. In this way, an impaction force can be applied to the cup to facilitate proper seating in a bone cavity (such as the acetabulum in the case of a hip joint).

Preferably, the drive plate is located on the same side of the jaw members as the cup component when the instrument is in use. The lugs on the jaw members will then face in generally the same direction as upstands on the jaw members, if present.

The guides should define a path for the jaw members to slide along which includes a radial component. It will be preferred for many applications that the jaw members slide radially. The angle between the paths along which jaw members slide and the radius will usually be not more than about 15°, for example not more than about 10°, especially not more than about 5°.

The number and arrangement of the jaw members should be selected to provide adequate support for the cup component. It will often be preferred for the jaw members to be spaced apart approximately uniformly around the instrument. For example, when there are two jaw members, it can be preferred for them to be arranged so that the angle between the paths on which they slide is about 180°. When there are three jaw members, it can be preferred for them to be arranged so that the angle between the paths on which the slide is about 120°. There can be more jaw members, for example four jaw members or five jaw members or six jaw members or more.

Each of the jaw members can include an upstand which is arranged so that it is directed towards the cup component when the instrument is in use. It will often be appropriate for the upstands to be directed in approximately the same direction, which might be approximately perpendicular to the direction along which the jaw members slide. This can help to minimise loads on the formations on the jaw members when an implantation force is applied to the cup component through instrument. When the upstands are intended to grip an internal surface of a cup component, it can be preferred for the cup engaging surfaces of the upstands to diverge slightly. When the upstands are intended to grip an external surface of a cup component, it can be preferred for the cup engaging surfaces of the upstands to converge slightly. The upstands might be provided with a lip to enhance the engagement with the cup component, especially if the cup component has a recess where it is gripped by the jaw members in which the lip can be received.

The instrument can include a drive shaft by which rotational movement can be imparted to the drive plate. A drive shaft can extend through a bore which extends through the body member of the instrument. The drive shaft can have a cranked handle by which it can be twisted to cause the drive plate to rotate. The drive shaft can be configured to be gripped by means of a powered drive unit. The drive shaft can have a universal joint or a constant velocity joint to facilitate driving the shaft from different angles.

The nature of the engagement between the instrument and a cup component depends partly on the design of the drive plate, in particular the pitch of the track. A relatively small pitch will mean that the jaw members are driven more slowly towards and away from the cup component, and the mechanical advantage which is obtained from the instrument will be greater. Conversely, a relatively large pitch will mean that the jaw members are driven more quickly towards and away from the cup component, and the mechanical advantage which is obtained from the instrument will be smaller. The pitch of the track should be selected to suit the requirements of a particular application with these factors in mind.

Separate tracks can be provided on the drive plate for the jaw members. However, it will frequently be preferred that just one track is provided on the drive plate. When two or more jaw members are driven using a common track, the formations on the jaw members should be offset relative to one another to accommodate the pitch of the track, so that the distance from the centre of the drive plate to the part of each of the jaw members which engages the cup component is approximately equal. For example, if there are three jaw members which are spaced apart equally around the drive plate, and the formation on one of the jaw members is provided at one end of the jaw member, the formation on the adjacent jaw member should be spaced apart from the end of the jaw member by a distance which is approximately equal to one third of the pitch of the spiral track.

The track on the drive plate can be a groove or a rib. When the track on the drive plate is a groove, the formations on the jaw members can be in the form of pins, which might be round or square in cross section, or in the form of short ribs. A formation in the form of a rib will preferably be rounded (for example so that it is approximated to radiussed) so that it can slide along the track. When the track on the drive plate is in the form of a rib, the formations on the jaw members might be in the form of short slots, which will preferably be rounded (for example so that it is approximated to radiussed) so that they can slide along the track.

The instrument can include a mechanism by which the torque which is applied to the drive shaft is limited when the jaw members engage the cup component through their upstands. This has the advantage that the force that is applied to a cup component through the jaw members is controlled, with sufficient force being applied to grip the cup component securely, and the force being limited so that neither the cup component nor the instrument is damaged. Suitable torque limiting devices are known. For example, when the torque exceeds a predetermined value, the connection between the applied drive and the drive plate can be decoupled. An example of a suitable torque limiting mechanism can include two parts which have cooperating pinion gears. Drive can be transmitted between the parts when the gears are meshed. The parts are biassed into engagement. In the event that the resistive torque exceeds a predetermined limit, the parts separate, overcoming the biassing force which causes the parts to engage with one another.

For some applications, it can be preferred to include a mechanism which restricts rotational drive to one direction, so as to prevent inadvertent drive in the opposite direction. The mechanism should be capable of being disengaged (to allow rotational drive in the opposite direction).

The instrument of the invention can be made from one or more metallic materials. Materials which are commonly used in the manufacture of surgical instruments for use in orthopaedic procedures are known. Suitable metallic materials include certain stainless steels. Parts of the instrument might be made from materials other than metals, for example polymeric materials.

Cup components that might be manipulated using the instrument of the invention might have a diameter of, for example, from about 40 mm to about 80 mm. The instrument of the invention might be arranged to manipulate cup components having a range of diameters of at least 15 mm, preferably at least about 20 mm, for example at least about 25 mm. the range of cup components that can be manipulated by an instrument is dependent on the size of the drive plate and the transverse dimension of the spiral track at its inner and outer ends. The jaw members should be capable of moving towards the wall of the cup component so as to engage its wall with sufficient force to prevent the cup component becoming detached inadvertently from the instrument during the procedure.

Embodiments of the invention will now be described by way of example with reference to the accompanying drawings, in which.

Figure 1:
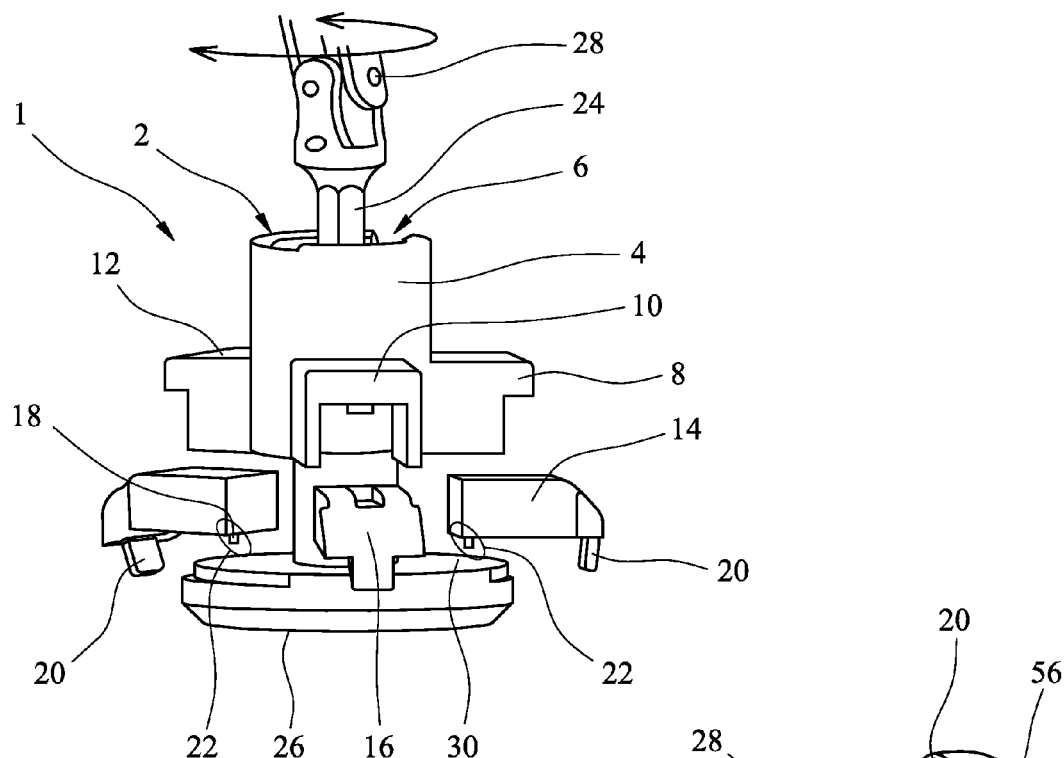
FIG. 1 is an exploded view of the cup engaging head of an instrument for gripping a cup component of an orthopaedic joint prosthesis in line with the invention.

Referring to the drawings, FIG. 1 shows the cup engaging head 1 of an instrument for gripping a cup component of an orthopaedic joint prosthesis, which comprises a body assembly 2 which is formed from a stainless steel material by a casting process. It has a core 4 which has a bore 6 extending through it. Three guide channels 8, 10, 12 extend radially from the core 4. The angle between each pair of the guide channels is about 120°.

The instrument includes three jaw members 14, 16, 18 which are dimensioned so that they are close sliding fit in a respective guide channel. Each of the jaw members has an upstand 20 at its outward end, and a formation 22 in the form of a pin which is circular in cross-section towards its inner end. The upstands on the jaw member can be inclined inwardly when they are intended to grip the external surface of a cup component.

The instrument includes a drive shaft 24 which extends through the bore 6 in the body assembly 2, and a drive plate 26 which is fitted to the end of the drive shaft so that it can rotate with the drive shaft relative to the body assembly. The drive shaft includes a universal joint 28 so that the drive shaft can be rotated from different directions.

The drive plate 26 has a spiral track 30 formed in the face which is directed towards the body assembly. The track is dimensioned so that the pins on the jaw members are a sliding fit in it.

Rotation of the drive plate by means of the drive shaft causes the jaw members to translate, due to the action of the spiral track on the pins and to the constraint on the movement of the jaw members which is provided by the guide channels. The constraint on the movement of the jaw members which is provided by the guide channels means that the movement of the jaw members is constrained to movement which within the guide channels, that is radial movement. The jaw members can be moved outwardly to engage the internal surface of a cup component so as to grip it, and then inwardly to release it.

The jaw members can be moved inwardly to engage the external surface of a cup component so as to grip it, and then outwardly to release it.

The distance between the cup engaging surface of each of the upstands and the axis of the instrument should be approximately equal. This can require careful positioning of the pin on each of the jaw members so that, in the case of a spiral which widens in a clockwise sense, the pin on a second jaw member, located adjacent to a first jaw member and spaced from it in a clockwise direction, is positioned further from the axis of the instrument by a distance which is equal to one third of the pitch of the spiral.

Figure 2:
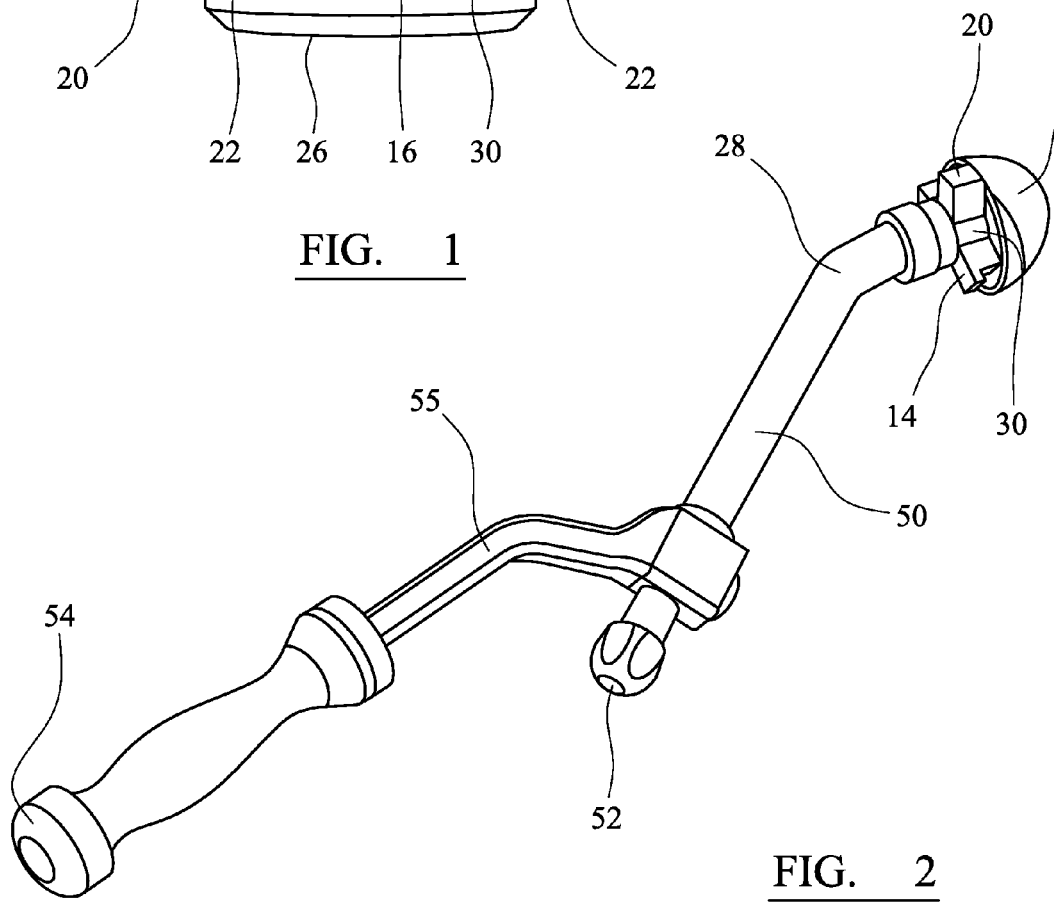
FIG. 2 is an isometric view of an instrument which includes the cup engaging head shown in FIG. 1.

FIG. 2 shows the instrument of the invention which includes the cup engaging head 1 shown in FIG. 1. The head is located at the end of an introducer shaft 50 which is hollow. The drive shaft 24 extends through the introducer shaft.

A control handle 52 is located at the proximal end of the introducer shaft and is connected there to the drive shaft 24. The control handle can be used to rotate the drive shaft within the introducer shaft, and so to rotate the drive plate 26 relative to the body assembly 2 of the cup engaging head.

The instrument includes an impaction arm 54 which is fastened to the introducer shaft towards its proximal end. The impaction arm has a plate 55 at its free end which can be used to apply a force to a cup component 56 which is engaged by the instrument. The impaction force is applied to the cup component through the body assembly and the jaw members. The drive plate is not affected when force is applied to the cup component. The impaction force can help to ensure secure engagement of the cup component in the body recess in which it is to be implanted, especially when it is to be secured in that recess using a bone cement material.

Figure 3:
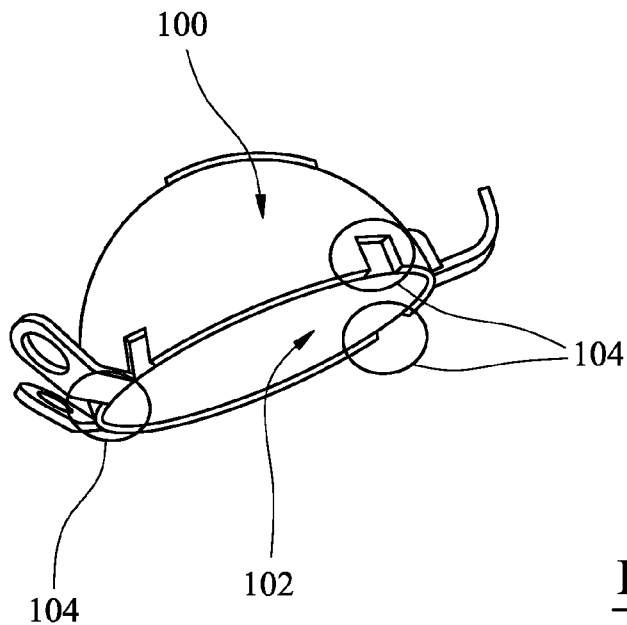
FIG. 3 is an isometric view of a cup component which is adapted for engagement using the instrument of the invention.

FIG. 3 shows a cup component 100 which has a spherical cavity 102 within it which provides a smooth bearing surface for articulation with a convex head component of a joint prosthesis. It is desirable to avoid contact with the bearing surface during a surgical procedure in order to minimise the risk that it might become scratched. The cup component has three recesses 104 provided in its external surface at its open edge. The recesses are configured to receive the ends of the upstands on the jaw members when the jaw members are moved inwardly as described above. The upstands are inclined inwardly so that they engage the recesses on the cup component, to retain the cup component on the instrument when the jaw members are deployed fully.

Figure 4:
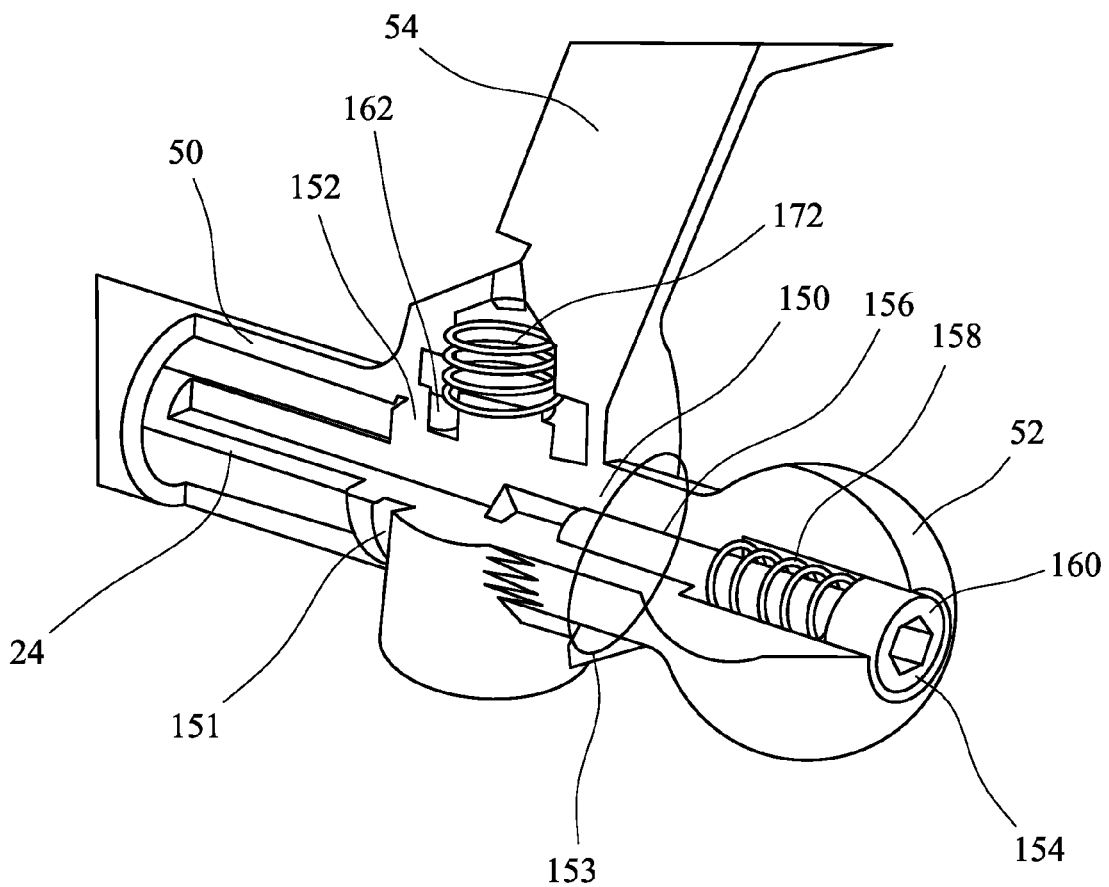
FIG. 4 is an isometric view, partially in section, through the drive handle of the instrument shown in FIG. 2.

FIG. 4 shows the mechanism within the introducer shaft 50 where the control handle 52 is connected to the drive shaft 24. The drive shaft has a sleeve 150 at its end whose diameter is wider than that of the shaft itself. The collar has an annular groove 151 formed in it. The drive shaft has gear teeth machined into the end face of the sleeve, in the region labelled 153 in FIG. 4. The control handle 52 has gear teeth machined into the end face which faces towards the sleeve on the drive shaft, in the same region 153. A connector bolt 154 extends through a bore in the control handle, into a threaded bore 156 in the sleeve 150 on the drive shaft 24. A helical spring 158 acts between the head 160 of the connector bolt and the end face of the bore in the control handle to urge the control handle against the sleeve on the drive shaft, so that the gear teeth on the end face of the control handle mesh with the gear teeth on the end face of the sleeve on the drive shaft.

When the gear teeth on the control handle mesh with the gear teeth on the end face of the sleeve, rotation drive can be imparted to the drive shaft using the control handle. When the torque that is applied to the drive shaft exceeds a predetermined value (for example when the jaw members are firmly in contact with a cup component), the control handle is forced away from the drive shaft against the biassing force of the spring 158, so that the gear teeth on the end faces of the control handle and the sleeve on the drive shaft disengage. The torque which causes the gear teeth to disengage in this way can be increased by tightening the connector bolt in the drive shaft, thereby compressing the spring.

The impaction arm 54 has a button 170 at its end where it engages the introducer shaft 50. The button is part of a button assembly which includes an arm 171 which extends around the sleeve 150 on the drive shaft to the side of the sleeve which is opposite is to the button itself. The arm has a pin 162 which is received in the annular groove 151 in the sleeve. The arm is acted on by a helical spring 172.

The mechanism shown in FIG. 4 includes a ratchet which provides a controlled resistance to rotation of the drive shaft. The ratchet is provided by a series of gear teeth 160 which are machined in the external surface of the sleeve 150 on the drive shaft and a tooth 174 on the arm 171, which is biassed towards the sleeve by means of the helical spring 172 so that it engages the teeth on the sleeve.

The action of the spring 172 on the arm of the button assembly causes the pin to sit in the groove on the drive shaft sleeve. This controls the axial position of the drive shaft within the introducer shaft. The spring also maintains the tooth 174 on the arm 171 of the button assembly in contact with the array of gear teeth on the external surface of the sleeve 150 on the drive shaft, providing resistance to rotation of the sleeve so as to prevent inadvertent rotation and consequent movement of the jaw members.

Depressing the button within the impaction arm causes the button arm to translate so that the pin on the button arm from the groove on the drive shaft sleeve. This allows the drive shaft to move axially within the introducer shaft 50, for example for disassembly of the instrument for cleaning purposes.

The invention claimed is:

1. An instrument for gripping a cup component of an orthopaedic joint prosthesis, the cup component having a cavity, comprising: a drive plate having a proximal face, the proximal face being configured to face away from the cavity when the instrument is in use, a distal face opposite the proximal face, and a spiral track formed in the proximal face; at least a first jaw member and a second jaw member, each of the first and second jaw members having a formation configured to engage the spiral track, and an upstand configured to extend distally beyond the distal face of the drive plate and engage the cup component; a body assembly, and at least a first guide and a second guide are carried on the body assembly, the first jaw member being slidingly engaged with the first guide, the second jaw member being slidingly engaged with the second guide, the body assembly has a bore, and a drive shaft extends through the bore and is connected to the drive plate; wherein when the formations of the first jaw member and the second jaw member engage the proximal face of the drive plate and the drive plate is rotated, the first jaw member and the second jaw member are caused to translate in the first guide and the second guide.

2. The instrument of claim 1, comprising a third jaw member and the body assembly carries a third guide.

3. The instrument of claim 1, wherein the track is provided as a groove in the proximal face of the drive plate.

4. The instrument of claim 1, wherein the first jaw member is at least partially disposed between the first guide and the drive plate, and the second jaw member is at least partially disposed between the second guide and the drive plate.

5. The instrument of claim 1, wherein the upstand and the formation on each jaw member are provided on a common face.

* * * * *